US006705984B1

(12) United States Patent
Angha

(10) Patent No.: US 6,705,984 B1
(45) Date of Patent: Mar. 16, 2004

(54) MUON RADIATION THERAPY

(75) Inventor: Nader Angha, Franksville, WI (US)

(73) Assignee: Maktab Tarighe Oveyssi Shah Maghsoudi, Burbank, CA (US)

( * ) Notice: Subject to any disclaimer, the term of this patent is extended or adjusted under 35 U.S.C. 154(b) by 596 days.

(21) Appl. No.: 09/783,078

(22) Filed: Feb. 15, 2001

(51) Int. Cl.$^7$ ............................................... A61N 5/02
(52) U.S. Cl. .................................................. 600/2; 7/3
(58) Field of Search ............................... 600/2, 1, 9, 3; 607/3, 1; 128/898

(56) References Cited

U.S. PATENT DOCUMENTS

| | | | | |
|---|---|---|---|---|
| 4,385,634 A | * | 5/1983 | Bowen | 600/407 |
| 4,504,438 A | * | 3/1985 | Levy et al. | 376/156 |
| 5,888,997 A | * | 3/1999 | Sessler et al. | 514/185 |
| 6,004,257 A | * | 12/1999 | Jacobson | 600/9 |
| 6,185,444 B1 | * | 2/2001 | Ackerman et al. | 600/410 |

OTHER PUBLICATIONS

David G. Nicholls, et. al., Bioenergetics 2, 1992, pp. 1–204, Academic Press, New York.
Wayne M. Becker, The World of the Cell, 1986, pp. 178–2 274, Benjamin/Cummings, Menlo Park, California .
Youssef Hatefi, The Mitochondrial Electron Transport and Oxidative Phosphorylation System, Ann. Rev. Biochem., 1985, pp. 1015–1069, 54, Annual Reviews.
Robert Roskoski, Jr., Biochemistry, 1996, pp. 121–133, W.B. Saunders, Philadelphia, Pennsylvania.
Peter C. Hinkle & Richard E. McCarty, How Cells Make ATP, Scientific American, 1978, pp. 104–123, 238:3, New York.
Paul G. Hewitt, Conceptual Physics, 1993, pp. 630–637, HarperCollins, New York.
Johann Rafelski & Steven E. Jones, Cold Nuclear Fusion, Scientific American, 1987, pp. 84–89, 257:1, New York.
David R. Lide, CRC Handbook of Chemistry and Physics, 1990, pp. 11–2–11–3, CRC Press, Boston.
H.R. Hulme & A. MCB. Collieu, Nuclear Fusion, 1969, pp. 19–25, Wykeham, London.
Wayltam M. Becker, The World of the Cell , 1986, pp. 12–15, Benjamin/Cummings, Menlo Park, California.
Eldon J. Gardner, Principles of Genetics, 1984, pp. 96, New York.
Frank Close, Too Hot to Handle: The Race for Cold Fusion, 1991, pp. 265–266, Princeton UP, Princeton, New Jersey.
Ralph H. Petrucci, General Chemistry: Principles and Modern Applications, 1985, pp. 389;483, Macmillan, New York.
Wayne M. Becker, The World of the Cell, 1986, pp. 150–173, Benjamin/Cummings, Menlo Park, California.
Wayne M. Becker, The World of the Cell, 1986, pp. 82–84, Benjamin/Cummings, Menlo Park, California.

(List continued on next page.)

*Primary Examiner*—Thomas Denion
*Assistant Examiner*—Daniel Robinson

(57) ABSTRACT

This invention relates to a novel idea for irradiating a patient with a beam of Muon ($\mu$) particles, which in the proton ($H^+$) rich environment of the blood and the cells catalyzes more fusions of the Hydrogen-Deuterium, Deuterium-Deuterium, and Deuterium-Tritium nuclei. Through local radiation of the related body part(s), the already existing fusion energy is accelerated within the particular body part(s), thus facilitating the treatment of diseases. Muon bombardment of the cells can be applied for the treatment of all kinds of conditions and injuries, including AIDS and other infectious diseases, all cancers, all varieties of internal and external injuries and internal disorders, weight loss, repairment and rejuvenation of all body organs, treatment of enzyme inhibition, all neurological disorders, including paralysis, all psychological disorders, all genetic disorders, all endocrine system disorders, and all musculoskeletal disorders.

20 Claims, 2 Drawing Sheets

OTHER PUBLICATIONS

John R. Reitz & Frederick J. Milford, Foundations of Electromagnetic Theory, 1960, pp. 124–127, Addison–Wesley, Reading, Massachusetts.

David E. Martin & John W. Youtsey, Respiratory Anatomy Physiology, 1988, pp. 89–92, C.V. Mosby, Washington, DC.

David E. Martin & John W. Youtsey, Respiratory Anatomy Physiology, 1988, pp. 130, C.V. Mosby, Washington, DC.

David E. Martin & John W. Youtsey, Respiratory Anatomy Physiology, 1988, pp. 177–179, C.V. Mosby, Washington, DC.

David E. Martin & John W. Youtsey, Respiratory Anatomy Physiology, 1988, pp. 200, C.V. Mosby, Washington, DC.

Wayne M. Becker, The World of the Cell, 1986, pp. 750–754, Benjamin/Cummings, Menlo Park, California.

Wayne M. Becker, The World of the Cell, 1986, pp. 722–749, Benjamin/Cummings, Menlo Park, California.

Wayne M. Becker, The World of the Cell, 1986, pp. 759–778, Benjamin/Cummings, Menlo Park, California.

Albert Szent–Gyorgyi, The Living State and Cancer, 1978, pp. 68–72, Marcel Dekker, New York.

Albert Szent–Gyorgyi, The Living State and Cancer, 1978, pp. 21–24, Marcel Dekker, New York.

Albert Szent–Gyorgyi, The Living State: With Observations on Cancer, 1972, pp. 108–109, Academic Press, New York.

* cited by examiner

MUON RADIATION THERAPY

TECHNICAL FIELD

Muon radiation therapy is a novel means for the treatment of AIDS and other infectious diseases, for treatment of cancers, for all varieties of internal and external injuries and internal disorders, for weight loss, for repairment and rejuvenation of all body organs, for treatment of enzyme inhibition, all neurological disorders including paralysis, all psychological disorders, all genetic disorders, all endocrine system disorders, and all musculosketetal disorders.

BACKGROUND ART

Muons are unstable nuclear particles, sometimes called Mu mesons.

(Muon $\mu \pm m \approx (9.1 \times 2 \times 10^{-31}$ kg) (200) and [$\mu$ charge]= $\pm 1.6 \times 10^{-19}$ C).

Muons may be generated as a by-product in a cyclotron. Muons have a mass which is close to 200 times the mass of an electron. One type of Muon, namely an elementary particle, has an electric charge equal to that of an electron, but is about 207 times more massive than the electron. These short-lived elementary particles are produced when primary cosmic rays, primarily containing very fast protons, collide with the Earth's atmospheric particles. The average Muon's' lifetime in its rest frame is $2.2 \times 10^{-6}$ seconds.

SUMMARY OF THE INVENTION

Muon radiation therapy is a novel means for the treatment of AIDS and other infectious diseases, for treatment of cancers, for all varieties of internal and external injuries and internal disorders, for weight loss, for repairment and rejuvenation of all body organs, for treatment of enzyme inhibition, all neurological disorders including paralysis, all psychological disorders, all genetic disorders, all endocrine system disorders, and all musculosketetal disorders. Through the Muon bombardment of the human body in the proton ($H^+$) rich environment of the blood and the cells' mitochondria, the beam of Muon particles catalyzes more fusions of the Hydrogen-Deuterium, Deuterium-Tritium, and Deuterium-Deuterium nuclei, thus providing our bodies with a substantially enhanced rate of cold fusion energy. The acceleration of cold fusion in any part of the patient's body through local Muon radiation treatment increases the local energy and the vital activity of the related patient body part.

Muons are generated in proximity to a patient, and the Muons thus generated are directed to pass through a specific body part, to aid in treatment of that selected body part.

DESCRIPTION OF THE PREFERRED EMBODIMENTS

Muon radiation therapy is a novel means for the treatment of AIDS and other infectious diseases, for treatment of cancers, for all varieties of internal and external injuries and internal disorders, for weight loss, for repairment and rejuvenation of all body organs, for treatment of enzyme inhibition, all neurological disorders including paralysis, all psychological disorders, all genetic disorders, all endocrine system disorders, and all musculosketetal disorders. Through the Muon bombardment of the human body in the proton ($H^+$) rich environment of the blood and the cells' mitochondria, the beam of Muon particles catalyzes more fusions of the Hydrogen-Deuterium, Deuterium-Tritium, and Deuterium-Deuterium nuclei, thus providing our bodies with a substantially enhanced rate of cold fusion energy. The acceleration of cold fusion of any part of the patient's body through local Muon particle treatment increases the local energy and the vital activity of the related patient body part.

A Muon, namely an elementary particle, has an electric charge equal to that of the electron; but is about 207 times more massive than the electron. These short-lived elementary particles are produced when a primary cosmic ray, containing very fast protons, collides with the Earth's atmospheric particles. The average Muon's lifetime in its rest frame is $2.2 \times 10^{-6}$ seconds (Lide, Editor, CRC Handbook of Chemistry and Physics, 71st Ed. CRC Press, 1990–1991). The muons' speed is very close to that of light c (=$3 \times 10^8$ m/s).

Figure 1:
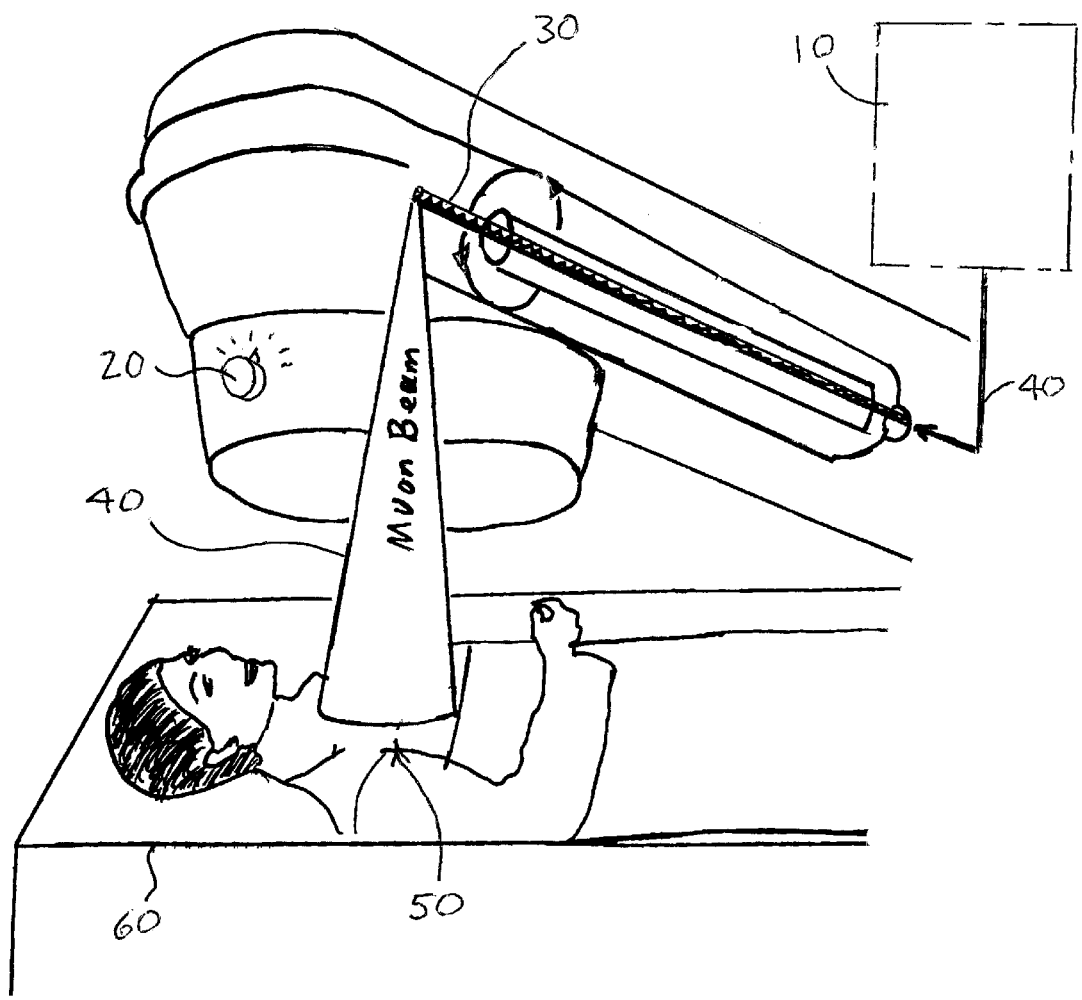
FIG. 1 is a schematic drawing of a patient being treated with Muon radiation therapy, wherein the Muon particle beams are movably directed to a selected body part of a patient for treatment.
Figure 2:
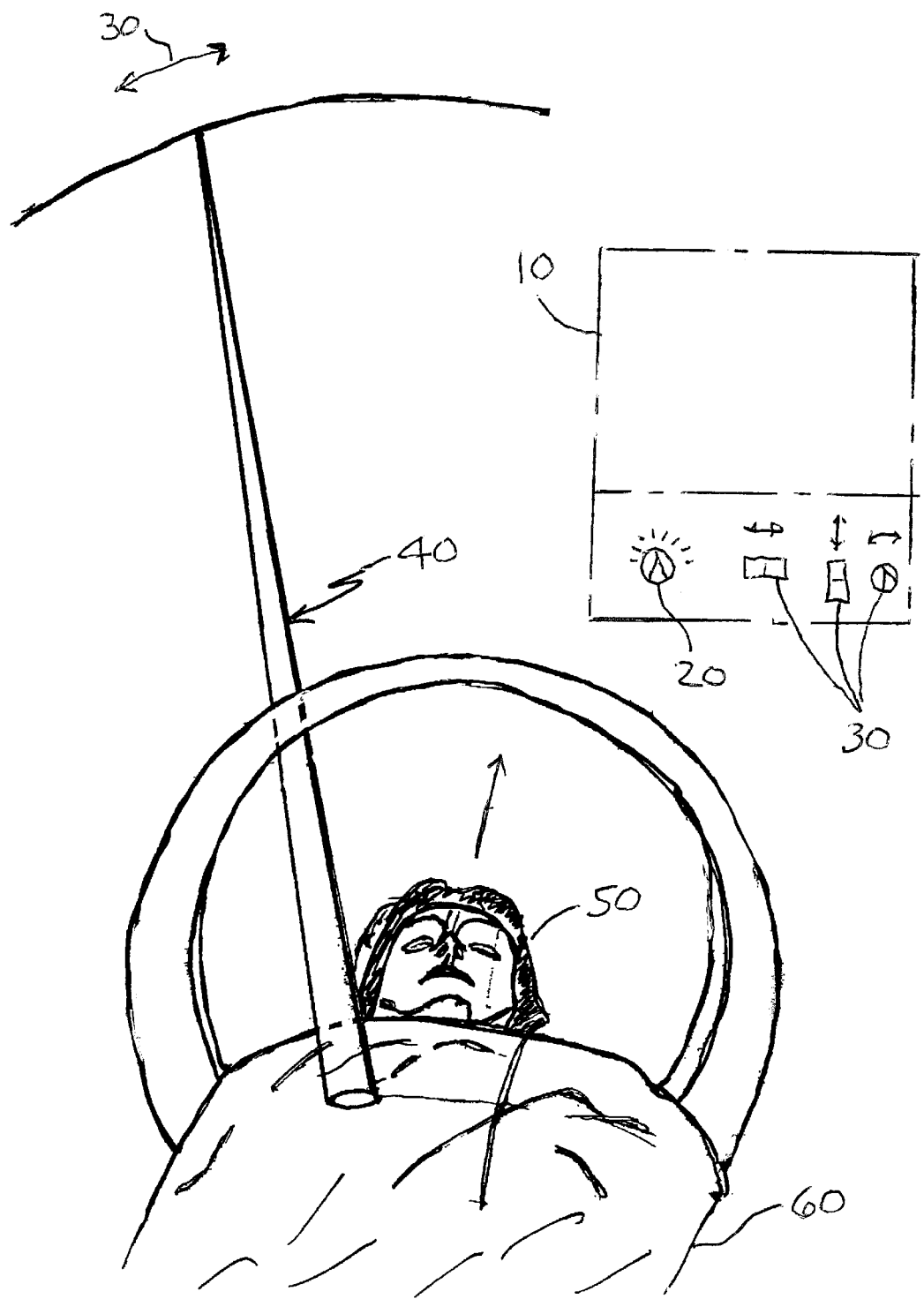
FIG. 2 is a schematic drawing of a patient being treated with Muon radiation therapy, wherein the patient is movably directed in relation to the Muon generator.

FIG. 1 and FIG. 2 each show a muon generating means 10 for generating a radiation beam of muons 40. One method of generating muon beams is with a cyclotron. Any known muon generating means may be adapted for use with this invention.

A selecting means 20 is provided for selecting the radiation intensity of the muons generated by the muon generating means 10. The selecting means 20 is used to select a predetermined radiation intensity from a range of 7000 curies of radiation to 9000 curies of radiation. A curie is a standard unit of radio activity, formally defined as the amount of radon in equilibrium with 1 gram of radium. The definition of a curie has been changed in recent years to mean an activity of exactly $3.7 \times 10^{10}$ disintegration's per second. The radiation intensity is selected depending upon the advancement level of the condition, e.g., cancer. Higher radiation intensity is selected for advanced levels of the condition, e.g., cancer, and lower radiation intensity is selected for less advanced levels of the condition, e.g., cancer. Any known selecting means 20 suitable for muon therapy may be adapted for use with this invention.

A directing means 30 is provided for directing a radiation beam of muons to a selected body part, as shown in FIG. 1. The directing means 30 is capable of moving back and forth in length and depth, and also preferably moves up and down in height, to adjustably position the directing means 30 in proximity to a selected patient 50 body part. Any known directing means suitable for use with muon therapy may be adapted for use with this invention. In this embodiment, the patient 50 is supported upon a suitable supporting structure 60.

Alternately, as shown in FIG. 2, the patient 50 may be moved in relation to the muon radiation beam 40, as is currently practiced with several other types of radiation therapy equipment. In this embodiment, the supporting structure 60 is moved to position the patient 50 in relation to the muon radiation beam 40.

We have come a long way towards understanding the chemical reactions that lead to Adenosine TriPhospate (ATP) production in mitochondria, choloroplasts, and bacteria. (Nicholls et al., Bioenergetics 2, Academic Press, California 1992; Becker, The World of the Cell, Benjamin/Cummings, Menlo Park, Calif. 1986; Roskoski, Jr., Biochemistry, W. B. Saunders, Philadelphia, Pa. 1996). Through these advances, the chemical chain reaction in the production of ATP seems to be well understood (Nicholls et al., 1992; Becker, 1986; Roskoski, 1996).

In spite of these advances, the actual ATP production mechanism, i.e., the very mechanism of respiration is most probably far from being thoroughly understood (Nicholls et al., 1992). We seem to comprehend the chemical processes leading to ATP synthesis. Yet, we have very little appreciation of how the initial energy produced by the oxidation of the carbohydrates is transferred from one stage to the other stage. Furthermore, we have yet to discover the energy needed for protons to be able to synthesize ATP.

Perhaps the most universally accepted theory for ATP production is the chemiosmotic theory suggested by Peter Mitchell in 1961 (Hatefi, Annual Review of Bio-chemistry, 54;1015 1985). His theory claims that the proton ($H^+$) density difference between the inside and the outside of the mitochondrion inner membrane produces the electrical potential energy that is needed to accelerate the protons leading to ATP production.

However, it is believed that Mitchell's theory ignores an important aspect in mitochondrion respiration by not properly addressing the source of energy, which drives the protons to the mitochondrion inter-membrane space and is therefore being primarily responsible for ATP synthesis.

Mitchell clearly and brilliantly explains the chemical processes through which protons are deposited in the inter-membrane space (Hatefi, 1985). However, the main source of energy leading to this deposition and subsequent protonation of the $F_0$–$F_1$ enzyme is overlooked (Nicholls et al., 1992; Becker, 1986; Roskoski, 1996; Hatefi, 1985). This leads me to agree that it is indeed the protonation of the "$F_0$–$F_1$ enzyme" which is responsible for ATP production. Nevertheless, I will show that the mere energy gained through the potential difference across the inner membrane is not adequate for the protonation of $F_0$–$F_1$ enzyme (or ATP synthesis).

THE WEAKNESSES OF MITCHELL'S THEORY

Many references in scientific literature indicate that the chemiosmotic theory is speculative, especially when it comes to the "Q cycle" of the electron transport (Hinkle et al., Scientific American, March 1978). There are at least two other deficiencies in Mitchell's theory as explained below.

The kinetic energy that the proton (produced by the breakdown of carbohydrates and subsequently delivered to $NAD^+$) carries is about 1.76 eV. Generally, protons, which are released into the matrix of the mitochondrion quickly dissolve in water and form molecules of Hydronium (Hy) $H_3O^+$. Taking the temperature of the matrix as T=310 K, then according to the kinetic theory of gasses, the average kinetic energy of each Hydronium ion is KE=(3/2)kT or 0.040 eV. Here, k (=$1.38 \times 10^{-23}$ J.molecule$^-$.K$^{-1}$)is the Boltzman constant. Thus, in the respiratory cycle, every time a proton is taken from the matrix, that proton has a kinetic energy of 0.040 eV. This happens five times in the respiratory cycle (Hinkle et al., 1978).

On the other hand, when ATP generation starts, the Electric Potential Difference (EPD) between the matrix and the inter-membrane space is about 0.22 V (Nicholls et al., 1992). Let us take the average EPD considerably lower (i.e., as 0.15 V). In this case, each proton, which has to be deposited in the intermembrane space, should have at least 0.15 eV of kinetic energy. Also, when the hydrogen atoms are ionized (Hinkle et al., 1978) at the exterior surface of the inner membrane, such ionization needs energy. The question is, where does the energy of ionization as well as the energy needed for the deposition of the protons into the inter-membrane space, come from?

The protons that are taken from the inside of the mitochondrion do not have enough kinetic energy (average KE=0.040 eV). Nor do they gain energy in their path to the inter-membrane space because their binding energy to flavin mononucleotide FMN and ubiquinone Q is released into the matrix (Hinkle et al., 1978). Furthermore, the mechanism of the hydrogen atom transfer from the matrix to the outer surface of the inner membrane is yet a mystery (Hinkle et al., 1978). Contrary to the general opinion, it is more convincing to conclude that the glucose breakdown energy is released into the matrix. It is largely spent on providing thermal energy for the system rather than being spent for ATP generation.

It is also hypothesized (Hinkle et al., 1978) that the kinetic energy of the protons gained through the inner membrane EPD, is spent on ATP synthesis (Nicholls et al., 1992; Becker, 1986; Roskoski, 1996; Hatefi, 1985). The EPD between the two faces of the inner membrane is about 0.22 V (Nicholls et al., 1992). Therefore, the kinetic energy gained by a proton through this EPD is 0.22 eV. Subsequently it takes two protons to synthesize one ATP; thus the total available energy is then 0.44 eV. In their collision with the inorganic phosphorous Pi, or the ADP molecule, the two protons transfer energy to them. More energy is transferred if we presuppose the protons collide with the inorganic phosphorous. Taking the initial speed of the Pi ($v_{iPi}$) equal to zero and applying the laws of conservation of momentum and kinetic energy, we can find the fraction of the energy that is transferred to the $P_i$. For elastic and inelastic collisions, the energy transferred to the $P_i$ is $4(M_{Pi}/m_H^+)(m_H^-/M_{Pi}+m_H^+)2KE_{H^+}$ and $(M_{Pi}/m_H^+)$ $(m_{H+}/M_{Pi}+m_H^+)2$ $KE_{H^+}$ respectively. Inasmuch as $M_{Pi} \sim 31 m_{H^+}$ and $KE_{H^+}=0.44$ eV, these energies amount to 0.048 eV and 0.012 eV; respectively. What Mitchell ignores is the fact that the two protons can contribute at most 0.048 eV to ATP synthesis; while ATP synthesis needs roughly 0.35 eV (approx. equivalent to 8 kcal/mol) (Becker, 1986; Roskoski, 1996). Therefore one ignored but important point is that, in an elastic collision between two protons and the $P_i$, each proton must have at least 1.45 eV of initial kinetic energy in order to transfer 0.35 eV to the $P_i$.

Based on these observations, Mitchell's theory disregards the fact that there is insufficient energy to transport the protons to the inter-membrane space as well as to synthesize ATP. These circumstances bring about the search for another source of kinetic energy for the protons. A source that provides enough kinetic energy for the protons to:

A) Channel through the enzymes,
B) Break themselves away from the electrons,
C) Push their way into the higher EPD of the inter-membrane space, and
D) On their way back into the matrix, through $F_1$–$F_0$ enzyme, have enough kinetic energy to synthesize and release ATP.

I contend that the only way to solve these questions, and perhaps other future questions, regarding the mechanism of ATP generation is to look at the occurrence of cold fusion in the mitochondrion. As I shall explain, this source (catalyzed cold fusion) increases the kinetic energy of the inside and outside matrix protons to higher values (almost 10 times more). Through enhancement of the naturally occurring rate of cold fusion in the mitochondria of the cells, we can treat diseases such as cancer, AIDS and all internal and external injuries.

Muon radiation therapy is a novel means for the treatment of AIDS and other infectious diseases, for treatment of cancers, for all varieties of internal and external injuries and internal disorders, for weight loss, for repairment and rejuvenation of all body organs, for treatment of enzyme inhibition, all neurological disorders including paralysis, all psychological disorders, all genetic disorders, all endocrine system disorders, and all musculosketetal disorders. Through the Muon particle bombardment of the human body in the proton ($H^+$) rich environment of the blood and the cells' mitochondria, the beam of Muon particles catalyzes more fusions of the Hydrogen-Deuterium, Deuterium-Tritium, and Deuterium-Deuterium nuclei, thus providing our bodies with a substantially enhanced rate of cold fusion energy. The acceleration of cold fusion of any part of the patient's body through local muon radiation increases the local energy and the vital activity of the related patient body part.

The Main Source of Energy in the Mitochondrion

As far as science has been able to ascertain, the protons are indeed taken from the inside and deposited on the outside of the inner membrane. Additionally, experimental evidence points out the fact that the passage of the protons through $F_1$–$F_0$ enzyme results in ATP release (Nicholls et al., 1992; Hinkle et al., 1978). Therefore, there must be enough energy for these processes to take place; the source of which has not yet been identified.

I assert that this source of energy is of nuclear origin; namely catalyzed fusion energy Rafelski et al., Scientific American, July 1987). Basically, the fusion of a proton ($H^+$) and a Deuterium (D) nuclei, or two Deuterium (D) nuclei, or a Deuterium and a Tritium nuclei within the mitochondrion or in the inter-membrane space is the main source of kinetic energy for the proton transfer and an eventual release of ATP.

The energy released in a D-D fusion is at least 3.26 MeV; which manifests itself in the form of the kinetic energy of the particles produced; e.g., neutrons (Rafelski et al., 1987). In the matrix of the mitochondrion and in its inter-membrane space, the fast moving products of the fusion collide with the H atoms and $H^+$ ions, and the enormous amount of kinetic energy from the products of the fusion is transferred basically to the hydrogen atoms and $H^+$ ions. This occurs because the proteins and enzyme molecules are much more massive than the hydrogen atoms or the $H^+$ ions (the protons) and therefore do not move nearly as fast. Then the $H^+$ ions will have enough kinetic energy to channel through the enzymes to the inter-membrane space. Their kinetic energy (gained through the collision with the fusion products; i.e., neutrons) will push them into the inter-membrane space against the EPD, and the collision of these $H^+$ ions with those in the inter-membrane space will bring about extended kinetic energy exchange. This observation demonstrates that during ATP synthesis the kinetic energy of the protons is much higher than approximately 0.22 eV. I concur that this is indeed the EPD between the matrix and the inter-membrane space responsible for the proton flow through $F_1$–$F_0$ knobs back into the matrix. I refer to the velocity gained through this EPD as the drift velocity. However, like electric conduction in wires, here the protons have thermal motion, and consequently thermal velocity gained through cold fusion energy release, as well. The consequences of this hypothesis could be numerous. However, before discussing this hypothesis any further, I would like to present a short review of catalyzed fusion.

Cold Fusion or Muon Catalyzed Fusion

The word fusion usually suggests to us the need for temperatures as high as those at the core of the sun, the powerful magnets, and electric charge plasma concentrated by powerful lasers (Rafelski et al., 1987; Hewitt, Conceptual Physics, Harper Collins, 1989). This ordinary type of fusion requires high temperatures. At high enough temperatures the kinetic energy of the $H^+$ ions is proportionally high. Thus, the electrostatic repulsion among the $H^+$ ions is not powerful enough to keep the protons apart and fusion takes place. The muon-catalyzed fusion, however, eliminates the need for high temperatures (Rafelski et al., 1987; Hewitt, 1989).

One type of muon, namely an elementary particle, has an electric charge equal to that of the electron; but is about 207 times more massive than the electron. These short-lived elementary particles are produced when primary cosmic ray, primarily containing very fast protons collides with the upper atmosphere. The average muon's lifetime in its rest frame is $2.2 \times 10^{-6}$ seconds (Lide, Editor, CRC Handbook of Chemistry and Physics, 71st Ed. CRC Press, 1990–1991). Ordinarily, this lifetime is not long enough for the muons to reach the earth's surface. However, since these muons' speed is very close to that of light c (=$3 \times 10^8$ m/s), the relativistic time dilation takes effect. Thus, according to the stationary observer on earth, the muons live much longer than $2.2 \times 10^{-6}$ sec. and they do indeed reach us.

F. C. Frank and Andrei D. Sakharov first suggested the muon-catalyzed fusion in the late 1940's. Commonly in the D atom the electron is relatively far away from the nucleus. The D atom is an isotope of the H atom. In the nucleus of the D atom there is a proton and a neutron. The laws of quantum mechanics indicate that the shortest possible radius of the electron in the D atom, i.e., the Bohr radius, is about $0.5 \times 10^{-8}$ cm. The faster (v-c) and 207 times more massive muon collides with the electron orbiting the D nucleus and knocks it off. It replaces the electron and forms Muonic Deuterium (MD). Quantum mechanics indicate that the radius of an orbit is inversely proportional to the mass of the orbiting particle. Once the electrons are replaced by negative Muons, the shortest orbital radius is reduced by a factor of 207; and consequently, MD is 207 times smaller than the D atom. This can be the key to the "cold fusion" of the Muonic atoms i.e., MD. The short orbital radius of the Muon makes the Muonic atom appear as a neutral particle to distant particles. At ordinary temperatures such a Muonic atom can collide with another Muonic atom to form a mumolecule (Rafelski et al., 1987). The nuclei of mumolecules are much closer to each other than they are in ordinary deuterium molecules. Thus, the fusion of these nuclei can and does take place at ordinary temperatures (Rafelski et al., 1987). This is due to the fact that the nuclei are close to each other and there is no need for high kinetic energies or high temperatures.

After fusion has taken place, the Muon is ejected in most cases. Thus, it is free to catalyze another fusion. The energy produced by the fusion is released in the form of kinetic energy of the neutrons; and these neutrons are in turn ejected as a product of the fusion. The product of the fusion of two MD atoms could be a Helium three, $^3He$ nucleus and a neutron. If the atoms in the mumolecule are an MD atom and a Tritium (T) atom, then the product of the fusion is an alpha ($\alpha$-) particle and a neutron. The T atom is an isotope of H with two neutrons and the $\alpha$- particle is the nucleus of the Helium four $^4He$ atom. The total time it takes for the muon to be captured and catalyze the fusion can be made less than a thousandth of the muon's lifetime (Rafelski et al., 1987).

The 3.26 MeV (1 eV is $1.6 \times 10^{-19}$ Joules) is the energy gained through one route of fusion. In fact, the fusion of D-D can produce $^3He$ or T. If T is produced, the gained energy is 4.03 MeV. Subsequently the T can fuse with another D to produce $^4$He and a neutron and 17.6 MeV. Accordingly, the average energy gained in, the H isotopes, fusion is 8.3 MeV.

Luis W. Alvarez et al. at Berkeley presented the first experimental evidence of muon-catalyzed fusion in the late 1950's (Rafelski et al., 1987). Since that time the physicists have continued working on theoretical and experimental muon-catalyzed fusion.

Cold Fusion in the Mitochondrion

The main part of the hard component cosmic rays, reaching the sea level, is composed of muons that have at least 2 GeV of energy. These muons obviously penetrate our bodies down to the cellular and even to the atomic level. There is a reservoir of hydrogen atoms and H$^+$ ions in mitochondria. The natural abundance rate of D to H is 1/6000 (Hewitt, Conceptual Physics, 1989). This means that in one mole of hydrogen there are as many as $6.02 \times 10^{23}/6000$ almost=$1 \times 10^{20}$ of D molecules. The existence of muons in the environment and the presence of the D atoms in the matrix of the mitochondrion inevitably mean that muon-catalyzed fusion could indeed take place in mitochondria. I maintain that this is the main source of kinetic energy for hydrogen atoms and protons in the mitochondria and I suggest the following mechanism for this process.

The Muons catalyze as many fusions as possible throughout their path in the mitochondria. In the next subsection we will see that the energy produced merely by this first stage of fusion is insufficient. However, one should note that the energy produced through each fusion is 8.3 MeV. This energy is released in the form of the kinetic energy of the ejected neutrons and the He nuclei produced through the fusion. Obviously, these fast particles could, and I believe they do, indeed catalyze many more fusions. This assumption, namely, that the products of the initial fusion catalyze further fusions is nothing new (Hulme, Nuclear Fusion, Springer-Verlag, New York 1969). In fact, it is known that in an environment of D atoms, fast neutrons can transfer part of their energy to the D atoms in a collision and harvest fusion. The problem in industry has been that the energy gained is insufficient to provide the D fuel as well as a usable economical surplus (Hulme, 1969). In essence, the rate of fusion and not its occurrence has been the problem.

Using Coulomb's law of electrostatic repulsion between the nuclei of two D atoms, one can calculate the energy needed to bring the nuclei together to a distance of $r_0$. If we take $r_0$ to be roughly the same as the nuclear radius, i.e., $r_0 = 5 \times 10^{-13}$ cm, then the energy of repulsion for two D nuclei is approximately 0.29 MeV. Furthermore, as we have mentioned, the average energy produced by a D-D fusion is 8.3 MeV. The fusion energy manifests itself as the kinetic energy of the neutrons and the He atom. Using the conservation laws of momentum and energy, one can show that in an elastic collision with a D nucleus at rest, these particles transfer as much as 89% of this energy (0.89×8.3=7.39 MeV) to the D nucleus. Using the conservation law of linear momentum, one can show that for inelastic collision of a neutron or an α- particle with a D nucleus the kinetic energy of the system after collision is not less than 0.33% of the available energy (0.33×8.3=2.7 MeV). These energies are from 9 to 25 times larger than that needed to fuse the D nuclei; hence we can expect a secondary fusion. These secondary products, I conclude, yield more fusions, and in fact a chain of fusion reactions takes place in our bodies.

The Possibility of Cold Fusion in the Mitochondrion

Let's assume that the daily-required energy for an average person is 2000 kcal (one nutritional cal is equivalent to one kcal). The efficiency of the respiratory mitochondrion metabolism is estimated to be at about 40% (Becker, 1986). This means that about 40% of 2000 kcal, i.e., about 800 kcal is spent for the production of ATP (Becker, 1986). The kinetic energy of five out of each six H$^+$ ions is released into the matrix before the enzymes FMN and Q absorb it. This kinetic energy is part of the energy produced from the breakdown of carbohydrates. Additionally, we noted that in order for the two protons to synthesize an ATP, each need to have a kinetic energy of about 1.45 eV. This energy is 1.23 eV more than the energy each proton gains through the inner membrane EPD (i.e., 0.22 eV). Additionally, the ionization energy of the bound hydrogen atoms (the energy necessary to push the protons against the 0.22 eV EPD and synthesize the ATP) should be provided by fusion. Let us assume that all of the energy needed for the synthesis of ATP is provided by fusion, making this the only consumed part of the energy produced by fusion. Therefore, the energy of the carbohydrate breakdown is not used for the ATP synthesis. This assumption does not invalidate the great importance of the carbohydrate breakdown. It merely says that carbohydrates (food) are necessary to provide the mitochondrion with hydrogen or the fuel that is needed for fusion. On the other hand, fusion is necessary to provide the protons with enough kinetic energy to cross the inner membrane and eventually produce ATP. Accordingly, this assumption gives an equal importance to both food and fusion for life maintenance.

For example, let us assume 1000 kcal/day is provided by fusion in an average size body. In this case, the amount of energy produced in one second (or the power produced) is 48.4 W. As mentioned earlier, the average energy released by the fusion of two D nuclei is 8.3 MeV. Hence, there must be as many as f=(48.4 W/8.3 MeV)=$3.64 \times 10^{13}$ fusions/sec occurring in an average size body. Taking the average diameter of an animal cell as 20 micrometers (Becker, 1986), and the average density of the cell as 1.72 g/cm$^3$ (Eldon et al., Principles of Genetics, John Wiley & Sons, 1984), we estimate the average number of the cells in the body to be about $1.2 \times 10^{12}$. With this estimation, we are to assume the average body mass to be 70 kg. If we consider the average number of mitochondria in a cell to be 100, we then estimate the total number of mitochondria in an average body to be $1.2 \times 10^{14}$. Comparing this number with the frequency of fusions needed in the body (f=$3.64 \times 10^{13}$ fusions/sec), we conclude that on the average, we should have one fusion per mitochondrion each second.

The number of particles in the hard component cosmic rays is about 200/m$^2$sec. If we assume that the surface area of an average body as 1.2 m$^2$, then the approximate number of Muons that an average body receives is 240/sec. Since the least energy the Muons contain is 2 GeV, and the energy needed for each fusion is 0.29 MeV, then each Muon ideally produces about 690 fusions. Thus, as many as 690×240= $1.656 \times 10^5$ fusions are resulted by the incoming Muons themselves. Using f(=$3.64 \times 10^{13}$ fusions/sec) needed in the body, we conclude that each neutron produced by Muon catalyzed fusion should itself cause about $2.2 \times 10^8$ (=$3.64 \times 10^{13}/1.656 \times 10^5$) fusions/sec. Assuming that this fusion is a chain reaction (i.e., each neutron product of fusion produces two new neutrons through catalyzing each fusion; $2^{28}$=$2.68 \times 10^8$), this frequency of fusions (f=$3.64 \times 10^{13}$ fusions/sec) can be obtained if each produced neutron goes through a maximum of 28 fusions. In essence, each Muon should bring about a tree of fusion that at most branches 28 times (29 times totally).

On the other hand, the average energy produced in a fusion is 8.3 MeV. Dividing this energy by that needed for the fusion of two D nuclei or a D and a T nuclei, i.e., 0.29 MeV, we obtain 28.6. This (28.6) is the average number of fusions that a neutron product of a Muon-catalyzed fusion can cause; and it is amazingly the same amount needed. Hence, it is reasonable to conclude that 48.4 W can be produced by fusion in the body.

One of the ways to check the occurrence of fusion is to check the rate of neutron production in the system, or neutron counting. The average number of fusion produced neutrons for each Watt of power is $1.42 \times 10^{12}$ (Close, Too Hot to Handle, The Race For Cold Fusion, Princeton University Press, Princeton, N.J. 1991). With a power value of 48.4 W, we can expect the number of resulting neutrons per second to be $6.87 \times 10^3$. One may wonder why do we not see nearly as many neutrons ejecting from our bodies. There is an explanation for this circumstance.

As calculated earlier, the expected frequency of $f(=3.64 \times 10^{13})$ fusion per second in the average human body translates into one fusion per second in each mitochondrion. It is my belief that, hydrogen atoms or protons, in the proton pool of the mitochondrion, absorb the neutron byproducts of the final fusions and form a D atom or a D nucleus. This absorption takes place mainly because there is a reservoir of H and $H^+$ in the mitochondrion.

Another product of fusion is He. Assuming each fusion in the body produces one He, then the number of He atoms produced in the body will be $3.64 \times 10^{13}$ per second. Taking the life span of a person to be 100 years, then the number of the He atoms produced through fusion in the body during our whole lifetime will be about $1.15 \times 10^{23}$. This is equivalent to 0.19 mol of He atom. Considering equal amounts of $^3$He and $^4$He in the body, the 0.19 mole of He is equivalent to 0.661 grams of He produced in one's body during his/her lifetime. Taking one's mass to be 70 kg, then the mass ratio of He by the end of one's life would be $9.44 \times 10^{-4}\%$. Taking into account the fact that air contains $5.24 \times 10^{-4}\%$ He by volume (Petrucci, 1982), the above percentage is certainly within the normal and acceptable range.

Enzymes

Biologists, biochemists, and biophysicists have overlooked the inevitable influence of cold fusion on enzyme activity. Careful and controlled experimental study of the behavior of enzyme activity as a function of the rate of cold fusion should prove beneficial.

The primary function of an enzyme is to absorb the specific substrate and establish a molecular order favorable to the intended chemical reaction. Establishing such an order implies a necessary reduction of the systemic entropy of the substrate molecules. From the thermodynamic equation $Q=-T\Delta S$, (Petrucci, Macmillan, New York 1982, Fourth Edition) a reduction in the entropy of the substrate system presupposes a flow of heat (or energy) into the substrate ensemble from the enzyme ensemble. This is because it is the enzyme, which brings order to the substrate system. Thus, the fact that the enzyme takes the substrate molecules and positions them in its active sites in such a manner that the appropriate surfaces are juxtaposed, implies an initial flow of energy into the substrate system. After the substrate molecules are bonded to the active sites of the enzymes, the substrate system is ordered and consequently less energy is needed to make the reaction take place.

Based on this it is my belief that enzymes do not in fact reduce the activation energy needed for a reaction. Instead enzymes give part of the activation energy to the substrate by bringing the molecules of the substrate into an order favorable to the reaction, thus orient them for the reaction. In this manner the energy that must be put into the system is reduced because the enzyme provides a portion of it. In essence, the stepwise flow of activation energy (in the presence of enzymes) has confused bio-scientists into thinking that somehow the same reaction requires less energy when the enzyme is present. The total activation energy is the same whether an enzyme is present or not; only the form and the stages of the energy flow into the reacting substrate molecules differ.

Considering this, the question then arises: What is the source, which supplies enzymes with the energy they transfer to the substrate? The enzyme, as previously discussed, invests energy into the substrate arranging and ordering the molecules in such a way as to predispose them to the intended chemical reaction. This is a repetitive process requiring energy on a continuous basis. The question then remains: Where does the energy needed for this function of the enzyme come from?

At this point we must remember that enzymes are composed of proteins, including all 20 amino acids (Becker, Benjamin/Cummings, Menlo Park, Calif. 1986). On the average, 55 percent of the atoms present in amino acids are H atoms ($H^+$ ions) (Becker, Benjamin/Cummings, Menlo Park, Calif. 1986). Therefore, comparatively speaking, there is a much larger number of H atoms present in an enzyme than in the substrate (e.g., ATP) or (generally) other molecules in the environment. Additionally, the large molecular mass number of proteins (about 50,000) contributes to the abundance of H atoms in enzymes. Considering these facts, I believe that enzymes are either the very sites where cold fusion of the $H^+$ ions with the other $H^+$ ions or D, or T nuclei takes place or, alternatively, they (enzymes) are the main recipients of the energy of cold fusion. Furthermore, cold fusion provides energy to the enzyme enabling it to elicit from the substrate ensemble the molecular order favorable to reaction.

In this fashion the enzyme supplies part of the activation energy of the reaction to the substrate molecules. Therefore, the enzyme-assisted hydrolysis of ATP is actually facilitated by cold fusion. Whether fusion occurs in the enzyme or not, the energy of the fusion (which manifests as the kinetic energy of the molecules of the environment) is transferred to the enzyme by the $H^+$ ions. Because these ions are the lightest particles present (other than electrons), they are the transporters of kinetic energy in the environment. Since enzymes are composed of hydrogen-rich molecules (proteins), they attract fusion energy. The kinetic energy gained by the enzyme in this manner is partially transferred to the substrate molecules; thus giving them more mobility resulting in the increased possibility of favorable juxtaposition of their appropriate surfaces. The active site of the enzyme is where the substrate molecules receive this kinetic energy.

In cases of enzyme inhibition, therapeutic treatment should consist of accelerating the rate of fusion in the body especially in the enzymes. This is made possible by limited bombardment of the body with Muon particles. A dosage of Muon particles accelerates the rate of cold fusion in areas where there are clusters of $H^+$ ions, e.g., enzymes. The "extra" energy produced in the enzyme as a result of cold fusion facilitates and increases its activity, which in turn lessens enzyme inhibition caused by agents such as drugs or poisons.

Nerve Cells

The most important factor in the transmission of the signal through the nerve and muscle cells is the random motion (as opposed to drift motion) of the ions in these cells. Similar to electrical conductors (i.e., wires) (Reitz et al., Addison-Wesley, Reading, Mass. 1962), the ions inside the nerve cell have a thermal (random) motion as well as a net drift motion. As I have hypothesized, this random motion is due to the kinetic energy gained through fusion of the H isotopes nuclei (roughly one fusion per mitochondrion per second). Any action potential gives a drift velocity to the ions. The presence of fusion is necessary in order to provide for the random motion to the ions. The decomposition of ATP can also accomplish this random motion; but this decomposition is achieved by enzymes, which gain energy through fusion. Therefore, either directly through the collisions or indirectly through the decomposition of ATP, fusion is responsible for the random motion of the ions in the cells including the nerve and muscle cells. The task of the electrical impulse is merely to stimulate the nerve or muscle cells and give a directional net component to the previously "random" motion of the ions. If the random motion does not exist then the $Na^+$ and $K^+$ will practically be frozen. In that case the ions' influx or outflow occurs much more slowly than what we see in the body. This means that the stimuli will be transmitted across the nerve cells very slowly and thus the nervous system would not work nearly as rapidly as it does. The random motion of the ions is vital to the function of the nervous system and that itself is a result of cold fusion. A careful and systematic study of the effect of a controlled Muon bombardment of the nervous system should reveal many new ways to enhance the activity of the nerves, especially in cases of paralysis. As in every other case we will start with the controlled animal studies to promote assurance of the effects.

Muscle Cells

As previously discussed, the "random" speed of the ions plays a major role in the conduction of the electrical signal throughout the body. Both anaerobic-aerobic synthesis of ATP and its hydrolysis are deeply dependent on the occurrence of cold fusion in the environment. Cold fusion in the body is in fact the main source of energy for muscular activity.

The consequences are enormous. The beating of the heart, the motion of blood through the veins and arteries, the expansion and contraction of the lungs, the digestive movement of the stomach, the gastrointestinal movement, and in general every movement of essential body organs originates with the occurrence of cold fusion of the $H^+$ and $D^+$ ions, or that of $D^+$ and $D^+$ ions, or that of $D^+$ and $T^+$ ions deep inside the muscle cells. Even cellular motion itself (which basically stems from the kinetic energy of the molecules inside the cell) is a result of cold fusion inside the cell.

In heavy work or athletic activity the $O_2$ supply aerobically breaks down the molecules of glucose and fat. In weight loss, my suggestion is that actually the fat molecules can be "burned" faster with an enhancement of the rate of cold fusion in the body. The enhancement of the rate of cold fusion increases the speed of ATP synthesis, which in turn speeds up the breakdown of fat, and thus a faster overall weight-loss.

The Immune System

Antibodies constitute a class of proteins called Immunoglobins (Ig). Immunoglobins constitute about 20% of the total plasma protein in the blood. As stated previously, about 55% of protein is composed of hydrogen atoms (or hydrogen ions and its isotopes). The basic antibody molecule consists of four polypeptide chains, two identical light chains and two identical heavy chains. The molecular mass of each light chain is 23000 and that of the heavy chain is 55000. Thus, in each antibody molecule there are about 2(12650+30250)= 85800 hydrogen ions and its isotopes.

The B cells and T cells undergo a rapid proliferation and differentiation. In view of the fact that this process of proliferation and differentiation requires energy—the more energy available, the faster this process occurs, I claim that cold fusion is the most important factor in this process. After all, cold fusion increases the kinetic energy of the molecules in the environment and the more energy the molecules have, the faster the processes take place.

I also believe that since the antibodies are such hydrogen-rich molecules, the rate at which cold fusion occurs in them is much greater than in their environment—just as in the case of enzymes. The kinetic energy given to the antibodies by cold fusion is the energy with which the antibody works against the antigens—that is, seeking and binding to the antigen. In the case of the T cells, once again their energy mainly originates from cold fusion and with this energy made available to them, they detect and directly eliminate the antigen.

Generally speaking, the energy of the development of all processes (in the body) is mainly provided by cold fusion. The manner in which this energy is spent, however, is greatly dependent on the organ and ultimately on its structural genetic code. Specifically, the energy of the development of T cells and B cells out of hematopoietic stem cells and their subsequent differentiation is provided by fusion. However, the specific program, i.e., the blueprint for their proliferation and differentiation should be a genetic code embedded mainly in the tissues where the proliferation and differentiation takes place.

The enhancement of cold fusion through limited Muon bombardment of the body, among other things, should increase the rate of the T cell and B cell proliferation and differentiation, especially in a patient whose body energy level has been depleted, i.e. an AIDS patient. Fusion provides the molecules with direct kinetic energy. This is similar to providing the system with 100% useable fuel rather than with a fuel (food) which the body first has to process in order to convert (only a small percentage of) into a useable form.

Fusion of Lungs and Blood

What is the source of energy (or work) for the expansion of the lungs during inspiration? Although some energy is pumped into the lungs during expiration, it can be shown that the net work done on the lungs for each respiration is not zero. Biologists assume that ATP hydrolysis is the source of energy for breathing. However the main source of energy for the multitude of the functions of the lungs is the muon-assisted fusion of the $H^+$, or D, or T nuclei. The molecular kinetic energy resulting from fusion is by far greater than that produced by ATP hydrolysis. The lungs contain at least 180 million alveolar type II cells within which, among other things, there is an abundance of mitochondria (Martin et al., Mosby, St. Louis 1988), the presence of which guarantees the occurrence of cold fusion.

The energy produced as a result of fusion manifests itself as the kinetic energy of the molecules existing in the environment. The type II alveoli and their abundant mitochondria are the ignition point of this energy. The increase in the molecular kinetic energy of the alveoli in part, manifests itself as an increase in the internal temperature and pressure of the lungs. As a result of this increased kinetic energy, the epithelial surface extends and, consequently, the lungs expand. The ideal gas equation is PV=nRT where P is the pressure, V is the volume, n is the number of moles, R (=8.314 J/g mol. K) is the gas constant, and T is the absolute temperature of the gas (Petrucci, 1982). Obviously the change in the kinetic energy of the molecules presented in the alveoli changes P, V, and T disproportionately so that a change in "n" is inevitable. Because the lungs form an open system, the inflow of air changes "n" so that the equation holds.

The expansion of the alveoli and consequently that of the epithelial surface concludes with the intake of air into the lungs. In the process of "normal" inspiration-expiration the net work done by the lungs on the environment is $4.68 \times 10^7$ ergs/minute (Martin et al., 1988). This amounts to $7.8 \times 10^5$ ergs/sec. About 65% of this work is done against the elastic inspiratory muscles and 35% is done against other frictional forces (Martin et al., 1988). There are approximately 180 million type II alveolar cells each containing approximately 100 mitochondria and approximately one fusion per one mitochondrion occurring per second each producing an average of 8.3 MeV of energy. Thus the energy of cold fusion in alveolar type II cells can be calculated to be approximately $2.39 \times 10^5$ ergs/sec. Considering that the total energy needed for respiration is $7.8 \times 10^5$ ergs/sec, the order of magnitude for the two energies is the same. If, on the other hand, we take the average number of mitochondria in the alveolar type II cells to be 327, then the energy produced by fusion is $7.8 \times 10^5$ ergs/sec; which is the same energy needed for respiration. Obviously, the muscle cells (which contain mitochondria) of the lungs are also a site of energy production for the expansion-contraction of the lungs.

The energy for the production of the surfactant could very well be provided by these fusions also. It is possible for the surfactant to decrease surface tension by speeding up its macromolecules and then transforming their speed (and momentum) to the surface molecules. This transfer of speed (or momentum) reduces the binding potential energy of the surface molecules, thus decreasing surface tension.

Similarly, fusion in the mitochondria of the macrophages is the main source of energy for the function of the macrophages, which keep the alveoli clean and sterile. Fusion also supplies the energy for rapid ingestion of cell debris. Fusion is the source of energy for the proliferation of macrophages as well. An individual's resistance to lung infections is also directly related to the number of properly functioning and circulating lung macrophages. Thus, the proper rate of fusion in the mitochondria of the macrophages is perhaps the most important parameter in prevention of lung infections. Macrophages, which have the highest metabolic rate of ingesting and digesting bacteria, must be supplied energy by fusion in their mitochondria.

The diffusing capacity of $O_2$ and $CO_2$ across the link between the alveocapillary membrane and alveolus is the essence of the gas exchange. Generally, one important parameter in the diffusion of a gas from one place to the other is the magnitude of the gas molecular speed relative to that of the other molecules in the environment. Fusion provides kinetic energy for $O_2$ and $CO_2$ molecules, thus facilitating their diffusion. In general, as the kinetic energy of the molecules increases, the time they spend in the state of local binding to one another decreases; thus the diffusion rate increases.

The composition of blood very much resembles to that of seawater (Martin et al., 1988). In fact, one could say that blood is an evolved form of seawater. For example, species like sponges survive perfectly well by having seawater percolate inside them thus allowing $O_2$ and nutrients to enter and $CO_2$ and wastes to exit the organism. In more advanced (animal) forms of life, blood takes the place of sea water in performing these functions and has evolved more highly developed functions as well.

The erythrocytes, leukocytes, and platelets are suspended in plasma. There are about $5.4 \times 10^9$ erythrocytes, $7 \times 10^6$ leukocytes, and $2.5 \times 10^8$ platelets in one cc of blood (Martin et al., 1988). Since the erythrocytes do not contain mitochondria, the mitochondrion cold fusion does not take place in them. Taking the average number of mitochondria in the leukocytes as 100 and the rate of cold fusion as one per second per mitochondrion, then the approximate energy produced in one cc of blood is 9300 ergs/second. The main function of the erythrocytes is to carry hemoglobin. Because the primary role of hemoglobin has long been assumed to be the transportation of $O_2$, its important role of $H^+$ transportation and containment has received much less attention.

Each minute a metabolizing cell consumes approximately 250 ml of $O_2$ and produces approximately 200 ml of $CO_2$. Plasma carries twice as much $CO_2$ as that carried by erythrocytes. The $CO_2$ metabolized by cells is carried either in a dissolved or a hydrated form; i.e., $H_2CO_3$ or combined with plasma proteins and hemoglobin. About 94% of $CO_2$ is carried in the bound or hydrated form. According to the equation:

$$H_2O + CO_2 \rightarrow H_2CO_3 \rightarrow H^+ + HCO_3^-$$

carbonic acid dissociates to $H^+$ and $HCO_3^-$. Many of the $H^+$ produced from this dissociation of carbonic acid then bond with hemoglobin and subsequently release a $K^+$. However, cold fusion can take place in erythrocytes during the time when the $H^+$ is, in fact free (Martin et al., 1988).

Thus, hemoglobin also carries $H^+$; which suggests the idea of fusion in hemoglobin itself. Consequently, in addition to the fusion energy produced in the mitochondria of the leukocytes, the presence of H+ in the erythrocytes produces additional fusion energy in blood.

On Medical Applications of Cold Fusion

The rate of cold fusion in cells and blood is determined by two factors. The first factor is the number of Muons per second in cosmic rays bombarding the body, and the second is the pH level of the system itself. The pH level also determines the rate of Muon production in the blood, or generally speaking, the body itself. Unknowingly, traditional medicine has limited treatment for physical diseases where the pH level of diseased organs is manipulated to enhance the rate of cold fusion.

Medication prescribed by a traditional doctor changes the acidity of the blood, thus changing the concentration of $H^+$ ions in the entire body. This latter parameter changes the rate of cold fusion, i.e., the body energy level. If the change is towards a more acidic environment (more $H^+$), then the rate of fusion increases and more energy is produced in the body. The availability of more energy to the body results in increased production of B and T cells, thereby strengthening its immune system. Since this process makes more energy available to cells in the entire body, they reach maturity more rapidly and divide more often.

The increased abundance of B and T cells, coupled with this accelerated rate of cell regeneration, enhances the body's ability to eliminate foreign organisms and damaged cells and replaces these damaged cells with healthy new ones. This process continues until such foreign organisms are sufficiently weakened and diseased cells are eliminated and replaced. The body then returns to its original balanced state and the person is termed "cured." Traditional medicine can thus be considered an attempt to control cold fusion in the body by means of the blood pH level manipulation, and consequently that of the cells. Medication could also affect the genetic code of the cells.

In order to fight some diseases, on the other hand, the body needs more energy or a higher rate of fusion than is available to it from this process alone. In fact, it is logical to assert that for a fixed number of Muons, the curve of fusion versus the number of the $H^+$ ions is asymptotic, i.e., it saturates beyond a certain number of $H^+$ ions. In this case no matter how much the number of $H^+$ ions or the pH of the environment is increased, the number of fusions in the cells is not going to increase. Consequently merely changing the pH level or administering medication cannot cure some conditions, e.g., cancer and AIDS.

To address this problem, modem medicine has turned to radiation therapy. Radiation therapy should attempt to manipulate the first parameter, which controls cold fusion in the body, namely, the rate of Muons bombarding the body per second. However, since the wrong particles, e.g. photons, are used, the rate of fusion does not increase sufficiently to eliminate the disease. Because of a lack of understanding of the occurrence and vitality of cold fusion in the entire body, traditional medicine has failed to use radiation therapy properly.

Obviously, we can (and should) increase the rate of fusion by bombarding the body and, consequently, body cells, with simulated Muons. Thus, my suggestion for a much less invasive and more rapid treatment of both internal and external injuries (next subsection), as well as diseases is Muon radiation therapy applied subsequent to administration of a medication, which increases the pH level of the body.

A characteristic deficiency in AIDS is lymphopenia, a marked reduction in the number of lymphocytes in the blood (Becker, 1986). This reduction manifests itself as a loss in the body's ability to maintain its immunity, hence becoming susceptible to a variety of diseases. In theory, reconstruction of the immune system would be an effective treatment (Becker, 1986). That is to say, the body must regain its balance in the production of B and T cells.

My suggestion for this "reconstruction of the immune system" is the bombardment of those body parts responsible for the production and conduction of lymphocytes, i.e., the long bones, the thymus, the spleen, the tonsils, and the lymph nodes, with high, controlled, dosages of Muons. This will enhance fusion at these sites thereby facilitating proliferation of B and T cells, the lack of which is the symptom of AIDS.

I believe, rather than looking for a medicinal cure for AIDS, we should seriously and systematically study the effects of Muon bombardment of the body. AIDS is one of the many diseases, which can be cured through Muon radiation treatment method.

The Injury Repair Mechanism and Fusion

Injuries to the body can be divided into external and internal ones. In both types of injuries, the mechanical damage is repaired by cellular substitution through fast cell division (Becker, 1986). This rapid division of cells at the site of damage has been the source of consternation for immunology. What triggers the onset of fast cellular reproduction at the site of damage? To answer this question, let us look at energy production in the blood and the specific means by which this production is enhanced. In the last sections it was demonstrated that the source of energy in the erythrocytes is cold fusion of $H^+$, $D^+$, and $T^+$ ions.

When an external injury occurs, the blood at the site of injury is exposed to the 02 in the air. The mitochondria in the leukocytes are therefore exposed to larger amounts of 02. This means that the rate of ATP generation in these mitochondria will accelerate; thus producing more $H^+$. This increase in the $H^+$ content of the mitochondria in turn increases the rate of cold fusion, which results in more energy in the cell. The rate of energy production in the cell is related to its rate of maturity. In essence, the increase in the rate of energy production in the cell will enhance the growth of the cell. The leukocytes at the site of the injury grow, thereby accelerating the cell cycle. The same happens to body cells around the site of the injury, i.e., due to enhanced fusion they too grow faster and subsequently experience an accelerated cell cycle.

A similar case can be made for the repair mechanism of internal injuries. Because the leukocytes in this instance are not exposed to any extra amounts of $O_2$ from the air, their rate of growth and division remains unchanged. On the other hand, the interior cells of an injured internal organ will be exposed to more body fluids including more $H_2O$ or $H^++HO^-$. Cold fusion among e.g. $H^+$ ions produces energy, which is then transferred by means of collisions to exposed cells thereby enhancing their growth and their division. Therefore, injuries can heal much more quickly when rapid fusion is induced at that location.

Experimental studies of the effects of cold fusion on the rate of repair and healing of injuries and internal disorders will indeed prove to be very enlightening. Perhaps such studies will begin to pave the way for a "space age" medicine in which our "modern" surgical techniques are relegated to primitive technologies. The effect of cold fusion on the rejuvenation of body organs and on the body as a whole also offers an avenue for careful investigation. I believe the primary difference between a "young" and an "old" organ lies in the rate of cold fusion taking place in each, the young organ having a higher rate of cold fusion than an old one. Exposing the injured organ to different dosages of laboratory-produced Muons can test the effects of cold fusion on both internal and external injuries and internal disorders.

A New Method of Cancer Treament

One of the diseases that human beings have not yet been able to successfully control and cure is cancer. Cancer is a disease characterized by uncontrolled cell proliferation. In the early 1920s Otto Warburg showed that the metabolism in cancerous cells is shifted towards fermentation (Becker, 1986). Albert Szent-Gyorgyi says (Szent-Gyorgyi, Marcel Decker, Inc., New York 1978): "Except for the most highly differentiated cells, such as those of the brain, animal cells have two states: the state of rest and the state of proliferation. I have called these states the alpha α and Beta β states. The state of proliferation is closely related to the state in which living systems existed before light and oxygen appeared. It makes all dividing cells similar to one another, and makes embryonic cells share many properties with the cancer cell. This proliferative state with its poor differentiation has higher entropy and lower free energy, which makes it the more stable state into which the cell tends to return. It is the ground state to which the cell will return when its organization is deranged. The cancer cell and the normal dividing cell differ mainly in their reversibility. The cancer cell is unable to rebuild its β state after it has completed its division and has to persist in its proliferative β state." He further explains the α state as follows: "When life originated some three billion years ago, our globe must have been a very unpleasant place, hot and pitch dark, being surrounded by a very heavy layer of water vapor. There was no light and no oxygen. This stage of biological organization I termed the "α state." At this stage the main function of living systems must have been fermentation and proliferation.

To be able to divide, the cell has to dismount its structure to a great extent. Also the oxidative mitochondria have to be disassembled, making the cell more dependent on fermentation for energy. All this means that the dividing cell has to differentiate and return, to an extent, to the α state. After completed division, the cell has to find its way back to the oxidative-resting β state."

According to Szent-Gyorgyi, the α state has a more liquid structure whereas the β state contains extensive semisolid structure (Szent-Gyorgyi, Marcel Decker, Inc., New York 1978). He also mentions: "We will understand cancer when we understand normal regulation, and we will understand normal regulation, when we can describe it in terms of the basic parameters, energy, entropy, and quantum rules." (Szent-Gyorgyi, Academic Press, New York 1972). He also discusses the fact that there is a lack of cohesive energy in cancerous cells (Szent-Gyorgyi, Academic Press, New York 1968).

I believe what happens in a cell to make it cancerous is the following: A) The cell's respiratory cycle stops due to lack of fusion in the mitochondria causing the cell revert to its fermentative state. B) As a result of the absence of fusion there is much less heat produced in the cell. The thermal motion of the molecules in the cell takes part in breaking off the water molecules. The lack of this thermal motion, however, means that there is more water in cancerous cells. This explains why cancerous cells have less viscosity or smaller cohesive energy and also indeed have a bigger volume than normal cells. C) The cell continues its ever proliferation in an attempt to regain its oxidative state. In fact, proliferation is the method that the cancerous cell adopts to fight the anomaly of lack of kinetic energy. It is a cure that the cell applies time and time again without success. This lack of internal energy also causes the free energy of the cancerous cell to be lower than that of normal cell.

In order to bring the cancerous cell back to its oxidative-resting β state, I believe we should facilitate fusion in the mitochondria of that cell. To achieve this goal I suggest the following: Instead of electromagnetic and other radiations, patients should be irradiated with Muon beams. This would increase the rate of fusion in all of the patient's cells including the cancerous ones. In addition, cancerous tissues should be exposed to $O_2$. The presence of $O_2$ in the mitochondrion leads to more oxidation of carbohydrates and this in turn increases the presence of $H^+$.

Finally, the presence of Muons and the abundance of $H^+$ ion the mitochondrion will facilitate fusion. This fusion provides the energy necessary for the respiratory cycle and thus the cell regains its oxidative-resting β state and ceases proliferation leading to the cure for cancer. My last suggestion is to increase the thermal energy of the cancerous cells. This can easily be done by the application of excessive local heat.

A laser beam is a very useful tool, because it is a concentrated beam. The thermal capacity of the human body is approximately $C=3500$ J/kg.C.°, and the average mass of a tumor, for example, is approximately m=20 grams. From the equation $Q=mC\Delta T$ we can see that an application of 3.5 Joules of energy will increase the temperature of the tumor by 50° C. This energy corresponds to an application of a 0.35 Watt laser for a period of 10 seconds. Hence, we would preferably use a laser with an output less than one Watt.

The laser safety guidelines of Cook County Hospital, specify that: Personnel shall not be exposed to light intensities above: (Direct setting) 1 micro-watt per square centimeter; (Indirect observing) 1 mili-watt per square centimeter; and (Diffuse reflected light) 2.5 watts intensity.

One important effect of thermal energy on the cancerous cell is to evaporate the water it contains or in general increase the molecular "random" speed. As a result of this so-called burning of the cell, there will be more ionization of $H_2O$ molecules in the cell. This along with an increase in collision rate leads to an abundance of both the $H^+$ ions and $O_2$ molecules both of which lead to the enhancement of fusion in the cell. The evaporation of the cell water content also results in an increase in the cohesive energy of the cell and reduce its liquidity, i.e., the cell approaches the β state. Therefore, I recommend local burning of the cancerous tumors as a very effective preliminary method to bring the cancerous cells back to the β state, i.e., to cure cancer. It is within the scope of this invention to cover any obvious modifications of the preferred embodiments described herein, providing such modifications fall within the scope of the appended claims.

What is claimed is:

1. A method of Muon radiation therapy treatment, comprising;
    applying a localized Muon radiation beam to at least a portion of a human body with predetermined doses of Muon particle beams, thereby catalyzing fusion of Hydrogen-Deuterium, Deuterium-Deuterium, and Deuterium-Tritium nuclei, thereby substantially enhancing a patient's body's rate of cold fusion.

2. The method of Muon therapy treatment of claim 1, comprising selecting a predetermined dose of Muon particle beams, selected from a range of: 7000 curie of radiation to 9000 curie of radiation.

3. The method of Muon therapy treatment of claim 1, comprising accelerating the cold fusion through localized Muon radiation, thus providing increasing local energy and vital activity of a treated patient body part.

4. The method of Muon therapy treatment of claim 1, comprising accelerating the limited bombardment of the body with Muon particles, thus providing for increasing the rate of fusion in the body, especially in the enzymes.

5. The method of Muon therapy treatment of claim 1, comprising burning glucose and fat molecules faster with an enhancement of the rate of cold fusion in the body, thus increasing the speed of ATP synthesis, and speeding up the breakdown of fat, resulting in a faster overall weight-loss.

6. The method of Muon therapy treatment of claim 1, comprising supplying energy by cold fusion to macrophages in their mitochondria.

7. The method of Muon therapy treatment of claim 1, comprising applying the Muon radiation therapy subsequent to administrating a medication, thus increasing the pH level of the body.

8. The method of Muon therapy treatment of claim 1, comprising bombarding selected body parts responsible for the production and conduction of lymphocytes with high, controlled dosages of Muons, thereby enhancing cold fusion and facilitating proliferation of B and T cells.

9. The method of Muon therapy treatment of claim 1, comprising rejuvenating a selected body organ with Muon radiation treatment, thereby increasing the rate of cold fusion taking place in said selected body organ.

10. The method of Muon therapy treatment of claim 1, comprising facilitating the presence of Muons and the abundance of $H^+$ in the mitochondrion, thus providing energy necessary for cancerous cells to regain its oxidative resting state, thereby ceasing excess cell proliferation.

11. The method of Muon therapy treatment of claim 10, comprising applying excessive local laser generated heat to cancerous cells not to exceed 10 miliwatt per second per square centimeter, thereby evaporating water within a cancerous cell, and increasing the cohesive energy of the cell while reducing its liquidity.

12. A method of Muon therapy treatment, comprising;
a Muon generating means;
a selecting means for selecting a predetermined dose of Muon particle beams;
a directing means for directing the Muon particle beams to a selected patient body part;
and a patient supporting structure, for supporting the patient during the Muon therapy treatment; the Muon particle beams for catalyzing fusion of Hydrogen-Deuterium, Deuterium-Deuterium, and Deuterium-Tritium nuclei, thereby substantially enhancing a patient's body's rate of cold fusion.

13. The method of muon therapy treatment of claim 12, comprising moving the directing means in relation to the patient, to bring the Muon particle beam to a selected patient body part location.

14. The method of Muon therapy treatment of claim 12, comprising moving the patient supporting structure in relation to the Muon particle beam to bring the Muon particle beam to a selected patient body part location.

15. The method of Muon therapy treatment of claim 12, comprising selecting a predetermined dose of Muon particle beams, thus providing sufficient kinetic energy for protons to channel through enzymes, breaking protons from electrons, pushing protons into higher EPD of inter-membrane space, and having enough kinetic energy to synthesize and release ATP within a patient treated by the Muon particle beams.

16. The method of Muon therapy treatment of claim 15, comprising burning glucose and fat molecules faster with an enhancement in the rate of cold fusion in the body, thus increasing the speed of ATP synthesis, and speeding up the breakdown of fat, resulting in a faster overall weight-loss.

17. The method of Muon therapy treatment of claim 12, comprising applying Muon particle beams to a patient subsequent to administering a medication, thereby increasing the pH level of the body.

18. The method of Muon therapy treatment of claim 12, comprising bombarding selected body parts responsible for the production and conduction of lymphocytes with high, controlled dosages of Muons selected from a range of from 7000 curies of radiation to 9000 curies of radiation, thus enhancing cold fusion and facilitating proliferation of B and T cells.

19. The method of Muon therapy treatment of claim 12, comprising facilitating fusion in the presence of Muons and increasing the abundance of $H^+$ in the mitochondrion, thereby providing energy necessary for cancerous cells to regain its oxidative resting state, and ceasing cell proliferation.

20. A method of Muon therapy treatment for immune deficiency syndrome and other infectous diseases, all cancers, all varieties of internal and external injuries and internal disorders, weight loss, repairment and rejuvenation of all body organs, enzyme inhibition, all neurological disorders including paralysis, all psychological disorders, all genetic disorders, all endocrine system disorders, and all musculoskeletal disorders, comprising;
applying a pre-determined dose of Muon particle beams to at least a selected portion of a human body, said predetermined doses of muon particle beams selected from a range of 7000 curies of radiation- to 9000 curies of radiation, thereby catalyzing fusion of Hydrogen-Deuterium, Deuterium-Deuterium, and Deuterium-Tritium nuclei, to substantially enhance a human body's rate of cold fusion.

* * * * *